United States Patent [19]

Jayasena et al.

[11] Patent Number: 5,869,641

[45] Date of Patent: Feb. 9, 1999

[54] HIGH AFFINITY NUCLEIC ACID LIGANDS OF CD4

[75] Inventors: Sumedha Jayasena, Boulder, Colo.; Kenneth A. Davis, Woodside, Calif.; Larry Gold, Boulder, Colo.

[73] Assignee: NeXstar Pharmaceuticals, Inc., Boulder, Colo.

[21] Appl. No.: 799,949

[22] Filed: Feb. 14, 1997

Related U.S. Application Data

[63] Continuation-in-part of Ser. No. 428,964, Apr. 25, 1995, which is a continuation of Ser. No. 714,131, Jun. 10, 1991, Pat. No. 5,475,096, which is a continuation-in-part of Ser. No. 536,428, Jun. 11, 1990, abandoned.

[51] Int. Cl.⁶ .......................... C07H 21/02; C12P 19/34; C12Q 1/68
[52] U.S. Cl. .......................... 536/24.31; 435/6; 435/91.2; 536/25.4; 935/77; 935/78
[58] Field of Search ...................... 435/6, 91.2; 536/22.1, 536/25.4, 24.31; 935/77, 78

[56] References Cited

U.S. PATENT DOCUMENTS

| | | |
|---|---|---|
| 5,270,163 | 12/1993 | Gold et al. . |
| 5,459,015 | 10/1995 | Janjic et al. . |
| 5,472,841 | 12/1995 | Jayasena et al. . |
| 5,475,096 | 12/1995 | Gold et al. . |
| 5,476,766 | 12/1995 | Gold et al. . |
| 5,496,938 | 3/1996 | Gold et al. . |
| 5,503,978 | 4/1996 | Schneider et al. . |
| 5,523,389 | 6/1996 | Ecker et al. ............... 536/23.1 |
| 5,527,894 | 6/1996 | Gold et al. . |
| 5,543,293 | 8/1996 | Gold et al. . |
| 5,567,588 | 10/1996 | Gold et al. . |
| 5,580,737 | 12/1996 | Polisky et al. . |
| 5,587,468 | 12/1996 | Allen et al. . |
| 5,595,877 | 1/1997 | Gold et al. . |

FOREIGN PATENT DOCUMENTS

| | | |
|---|---|---|
| 2 183 661 | 6/1987 | United Kingdom . |
| WO89/06694 | 7/1989 | WIPO . |
| 92/14843 | 9/1992 | WIPO ........................... 435/6 |

OTHER PUBLICATIONS

Stein et al. (1991) J. Acq. Immune Defic. Synd. 4:686–693.
Matsukura et al. (1989) Proc. Natl. Acad. Sci. USA 86:4244–4248.
Stein et al. (1993) Antisense Res. Dev. 3:19–31.
Joyce (1989) Gene 82:82–83.
Joyce & Inoue (1989) Nucleic Acids Research 17:711.
Ellington & Szostak (1990) Abstract of papers presented at the 1990 meeting on RNA Processing, Cold Spring Harbor Laboratory, Cold Spring Harbor, NY, p. 84.
Kinzler & Vogelstein (1989) Nucleic Acids Research 17:3654.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Thiesen & Bach (1990) Nucleic Acids Research 18:3203.

*Primary Examiner*—Stephanie W. Zitomer
*Attorney, Agent, or Firm*—Swanson & Bratschun L.L.C.

[57] ABSTRACT

Methods are described for the identification and preparation of high-affinity nucleic acid ligands to CD4. Included in the invention are specific 2'F RNA ligands to CD4 identified by the SELEX method.

1 Claim, 4 Drawing Sheets

HIGH AFFINITY NUCLEIC ACID LIGANDS OF CD4

This application is a Continuation-in-Part of U.S. patent application Ser. No. 08/428,964, filed Apr. 25, 1995, entitled "Nucleic Acid Ligands", which is a Continuation of U.S. patent application Ser. No. 07/714,131, filed Jun. 10, 1991, entitled "Nucleic Acid Ligands", now issued as U.S. Pat. No. 5,475,096, which is a Continuation-in-Part of U.S. patent application Ser. No. 07/536,428, filed Jun. 11, 1990, entitled "Systematic Evolution of Ligands by Exponential Enrichment", now abandoned.

FIELD OF THE INVENTION

Described herein are methods for identifying and preparing high-affinity Nucleic Acid Ligands of CD4. The method utilized herein for identifying such Nucleic Acid Ligands is called SELEX, an acronym for Systematic Evolution of Ligands by EXponential enrichment. This invention includes high affinity Nucleic Acid Ligands of CD4. Further disclosed are RNA ligands to CD4. Also disclosed are 2'-F RNA ligands of CD4. The oligonucleotides of the present invention are useful as pharmaceuticals or diagnostic agents.

BACKGROUND OF THE INVENTION

Structure

Mature CD4 is a 55 kDa monomeric glycoprotein found primarily on a subset of T cells. Other cells that express CD4 include monocytes, macrophages and Langerhans' cells. The molecule consists of an extracellular region (370 aa), a hydrophobic transmembrane domain (26 aa) and a highly charged cytoplasmic domain (38 aa). The cytoplasmic domain is strongly conserved across the species of mammals. The extracellular and transmembrane region show about 55% homology between mouse and human (Maddon, et al., 1987; Littman, 1987). The extracellular region consists of four tandem domains (V1–V4) with sequence and predicted structural homology to immunoglobulin variable-joining (VJ-like) domains (Maddon, et al., 1985), and hence the protein has been classified as a member of the immunoglobulin gene family. The crystal structure of soluble CD4 (the extracellular region) shows a rod-like structure having a length of 125 Å with a diameter of 25–30 Å (Kwong, et al., 1990; Wang et al., 1990).

Function

CD4 functions as an accessory molecule involved in the interaction between CD4$^+$ T cells and antigen presenting cells (APC) that express MHC class II proteins. Thus CD4 functions as an adhesion molecule increasing the probability of aggregate formation between T cells and accessory cells (Doyle & Strominger, 1987). In addition to its role in cell adhesion, CD4 also acts as a coreceptor for the TCR/CD3 complex contributing to its signal transduction function. Several studies have shown that CD4 and CD3 undergo comodulation (Saizawa et al., 1987; Anderson et al., 1988) as well as coclustering (Kupfer et al., 1987) upon T cell activation. A model advanced that is consistent with these results is that there is a formation of microclusters within the cell membrane consisting of CD4 and TCR/CD3. According to this model, bispecific antibody constructs will allow the formation of microclusters and thereby activation of T cells. This was experimentally demonstrated by using bispecific antibody constructs capable of crosslinking CD3 and CD4 to activate T cells (Emmrich et al., 1986, 1987).

Anti-CD4 antibodies

At least 25 different epitopes on CD4 have been postulated, and therefore the effect of any one antibody that binds to a specific epitope will be different from the effect of a second antibody targeted to a different epitope. Consequently, the effect of different monoclonal antibodies binding to CD4 differs with regard to mobilization of intracellular calcium when crosslinked to CD3, or to inhibition of anti-CD3 mediated stimulation. Anti-CD4 antibodies are able to block an antigen-stimulated T cell activation by: (1) inhibiting adhesion to accessory cells; (2) preventing microcluster formation between CD4 and TCR/CD3; and (3) exerting a negative signal. Anti-CD4 antibodies have been found to be most useful in inhibiting the initiation of T cell activation in resting T cells rather than the inhibition of activated T cell functions. Current understanding of the function of anti-CD4 monoclonal antibodies comes mainly from studies carried out with murine anti-CD4 monoclonal antibodies.

Effects of Anti-CD4 Antibodies:

On lymphocytes

Most monoclonal antibodies induce severe CD4-selective lymphocyte depletion in blood, spleen and lymph but not the thymus after single antibody injection. The depletion persists for about 10 days and starts recovering and reaching completion after 4–6 weeks.

On antibody response

Monoclonal antibodies to CD4 inhibit primary and secondary antibody responses of IgM and IgG classes. This immunosuppressive effect is effective if the antigen is injected after anti-CD4 antibody treatment. The antigen injection can be delayed for up to 15 days after the antibody treatment (Goronzy et al., 1986).

On cell-mediated immunity

Anti-CD4 monoclonal antibodies suppress delayed-type hypersensitivity reactions in normal as well as in C5-deficient mice, suggesting that complement is not a requirement (Kelley et al., 1987). Anti-CD4 monoclonal antibodies also inhibit the appearance of CD8$^+$ cytotoxic T cells against allogenic cells and virus infected cells (Woodcock et al., 1986; Weyand et al., 1989). Prolongation of renal allograft survival in monkeys using murine and human CD4 monoclonal antibodies has been described (Jonker et al, 1985, 1987; Cosimi et al., 1991).

Induction of tolerance

A unique property of certain anti-CD4 antibodies is their ability to induce immunological tolerance to both soluble and cellular antigens. However, this capacity is not a general feature of all anti-CD4 antibodies. Non-depleting anti-CD4 antibodies have induced tolerance in mice against human and rat immunoglobulins and allergenic bone marrow and skin grafts (Qin et al., 1990). Maintenance of the tolerance state to soluble antigens requires repeated injection, a condition which is not required for skin allografts that are not cleared like soluble antigens. The necessity of continuous antigen exposure probably indicates the involvement of T cells recently emerged from the thymus, since adult thymectomized mice remain tolerant to soluble antigens without reinforcement. The mechanism of anti-CD4 antibody induced tolerance is unclear.

In addition to the induction of tolerance, certain depleting anti-CD4 monoclonal antibodies do not sensitize, i.e., a rat monoclonal antibody does not elicit an antibody response in mice (Cobbold et al., 1984). The lack of sensitization is not directly due to immunosuppression, since it persists 42 days after injection of the antibody, after the time the mice have already recovered from immunosuppression (Benjamin & Waldman, 1986).

Anti-CD4 antibodies as a therapy in autoimmune diseases
Animal models

In general, anti-CD4 monoclonal antibodies may inhibit the onset or even stop the course of experimental autoimmune diseases.

Murine Diabetes

The most studied spontaneous experimental model of insulin dependent diabetes mellitus (IDDM) is based on nonobese diabetic (NOD) mice. In this model, diabetes occurs in females at 4–6 months of age and is preceded by a long phase of clinically silent insulitis (T cell infiltration of the islets). The infusion of purified T cells derived from a diabetic mouse spleen to syngeneic recipients transfers the disease. The diabetes pathogenesis involves both CD4 and CD8 cells, since in vitro elimination of these cells at the time of transfer eliminates the disease transfer (Bendelec et al., 1987). A large proportion of diabetogenic T cell clones (capable of transferring the disease) expresses the CD4 phenotype (Haskins et al., 1989).

Certain Anti-CD4 antibodies prevent the onset of IDDM when the treatment is initiated at 3 months, provided that the injections are repeated weekly (Charlton & Mandel, 1988; Hayward et al., 1988). However, in the weeks following the cessation of therapy, reinfiltration of islets may occur without diabetes (hyperglycemia). NOD mice treated before the onset of insulitis (about 2 weeks) do not develop insulitis and diabetes (Koike et al., 1987).

Murine lupus erythematosus

Weekly injections of anti-CD4 monoclonal antibodies at the age of 4 months (i.e., prior to the onset of overt autoimmune disease) to NZB X NZW F1 mice reduced the titre of anti-DNA antibodies and prevented the onset of glomerulonephritis and renal failure (Wofsy & Seaman, 1985) with a clear prolonged survival time. More importantly, anti-CD4 monoclonal antibody therapy is still efficacious when started after the time of disease onset when high anti-DNA antibody titres and proteinuria are observed (Wofsy & Seaman, 1987). This result is directly relevant to therapy in humans.

Other Experimental Diseases

Waldor et al., 1985, demonstrated that anti-CD4 monoclonal antibodies could prevent the development of experimental allergic encephalomyelitis (EAE) in the mouse and the rat.

Treatment with anti-CD4 monoclonal antibodies in experimental allergic myasthenia gravis has been shown to inhibit the disease (Christadoss & Dauphinee, 1986). The incidence of collagen type II induced arthritis in DBA/1-mice was also significantly reduced by the administration of anti-CD4 monoclonal antibodies (Hom et al., 1988).

Anti-CD4 antibodies in clinical studies

The prevention and successful treatment of various autoimmune diseases in experimental models by anti-CD4 antibodies have encouraged the use of such reagents in clinical trials.

In Rheumatoid Arthritis

The first clinical trial including anti-CD4 monoclonal antibodies was done in a group of patients with rheumatoid arthritis (Herzog et al., 1987). After 7 consecutive days of treatment (10 mg of Antibody/day), 37 out of 46 patients showed improvement with respect to the number of swollen joints, pain, and Ritche's articular index. However, the level of rheumatoid factor and immune complex treatment did not change during or after the treatment. With a different anti-CD4 antibody, similar clinical efficacy as well as a significant decrease in total immunoglobulin levels, decreased levels of the rheumatoid factor and decreased levels of erythrocyte sedimentation rate were observed.

In these clinical trials, clinical responses were observed immediately after the treatment and lasted for more than 3 months. Even though these antibodies were murine in origin, they were well tolerated with low side effects and no noticeable immune suppression. Unlike in animals, no profound immunosuppressive effect has been seen in humans upon exposure to anti-CD4 antibodies (Dhiver et al., 1989). More than 50% of the patients who received mouse anti-CD4 antibodies developed low titre human anti-mouse antibody (HAMA) response. Partially humanized antibodies have also been tried in clinical trials with rheumatoid arthritis patients, and have been shown to be effective (van der Lubbe et al., 1991).

In transplantation

The pivotal role played by $CD4^+$ T cells in allograft rejection was demonstrated in a mouse model (Cobbold et al., 1984; Madsen et al., 1987; Shizuru et al., 1990), and therefore represents a reasonable target for monoclonal antibody-based immunotherapy. The pretransplant injection of a murine anti-CD4 monoclonal antibody to rats selectively depleted 80–90% of peripheral $CD4^+$ T cells and induced donor-specific tolerance of cardiac allografts (Shizuru et al., 1990). However, in nonhuman primates the clearance of peripheral $CD4^+$ T cells was minimal as a result of delayed allograft rejection (Cosimi et al., 1990). The discrepancy between the rat and primate model may stem from the generation of an anti-murine response in primates due to the relatively distant phylogenic relationship. To overcome the anti-murine response in primates, murine antibodies have been humanized and such antibodies have been shown to be effective in the Cynomolgus renal allograft model (Powelson et al., 1994).

Initial attempts in using anti-CD4 antibodies in clinical trials were made in patients undergoing kidney transplantation (Morel et al., 1990) and the results are encouraging for further use of anti-CD4 antibodies in the management of rejection crises (Sabilinski et al., 1991).

CD4 as a viral receptor

Human immunodeficiency virus (HIV) utilizes the CD4 molecule as a mode of entry to infect T-helper cells. It has been shown that the envelope glycoprotein of HIV, gp120, binds with high affinity to the V1 domain of CD4 (Dalgeish et al. 1984; Maddon et al. 1986). Extensive genetic and biochemical analyses have shown that gp120 binds to a 12 amino acid region encompassing the predicted c'c" loop which is analogous to the CDR2 (complementary-determining region) loop of an immunoglobulin. HIV infection is associated with the progressive decline of $CD4^+$ T-cell subset (DeWolf et al. 1988). The decline of $CD4^+$ T-helper cells could be due to the result of either virus-induced cell killing or CD4 down modulation in HIV-infected cells by viral gene products. As the absolute $CD4^+$ cell count declines below $400/mm^3$, most patients show symptoms of AIDS. Thus, the absolute CD4 count is being used as a surrogate marker for the disease progress of HIV-infected individuals.

Anti-CD4 monoclonal antibodies as diagnostic agents

Anti-CD4 monoclonal antibodies are being used extensively to identify the T-helper subset in lymphocyte populations—especially in HIV-infected individuals—to follow disease progression and to obtain the decision point for initial anti-viral therapy (National Institute of Health, 1990). In addition, they have been useful in identifying T-cell activation (Maino et al. 1995). The preferred technique for using such antibodies has been multiparameter flow cytometry, where antibodies conjugated to different fluorophores are used.

Oligonucleotide ligands that bind CD4

Compounds having a polyanionic nature—such as sulfated polysaccharides (Weaver et al., 1990, 1992; Lederman et al. 1989), and dyes, like evans blue and tryphan blue (Balzarini et al. 1986)—have been shown to inhibit the binding of the HIV virus to T cells, and thereby the inhibition of virus-induced syntcytium formation. Oligonucleotides, being polyanionic, have also been shown to be inhibitory in viral entry (Matsakura et al. 1989 and references thereof). Although no complete and thorough study has been done to investigate the sequence specificity of oligonucleotides interfering with the gp120-CD4 interaction, the inhibitory effect has been shown to be length dependent (Stein et al. 1991). Oligonucleotides bearing phosphorothioate linkers in place of the regular phosphodiester linkage have identical charges, yet regular phosphodiester oligonucleotides do not inhibit syncytium formation. Compared to phosphodiesters, phosphorothioate oligonucleotides are nuclease resistant, a feature that is relevant to cellular assays. Phosphorothioate oligonucleotides, specifically a 28-mer consisting of cytosines (sdC28), bind both gp120 and CD4 with Kds in the $\mu$M range (Stein et al., 1993). Phosphorothioate oligonucleotides bind to these two proteins as evidenced by experiments using oligonucleotides derivatized with an alkylating agent as a probe.

SELEX

A method for the in vitro evolution of Nucleic Acid molecules with highly specific binding to Target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931,473, filed Aug. 17, 1992, entitled "Nucleic Acid Ligands," now U.S. Pat. No. 5,270,163 (see also PCT/US91/04078), each of which is herein specifically incorporated by reference. Each of these applications, collectively referred to herein as the SELEX Patent Applications, describes a fundamentally novel method for making a Nucleic Acid Ligand to any desired Target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the Target under conditions favorable for binding, partitioning unbound Nucleic Acids from those Nucleic Acids which have bound specifically to Target molecules, dissociating the Nucleic Acid-Target complexes, amplifying the Nucleic Acids dissociated from the Nucleic Acid-Target complexes to yield a ligand-enriched mixture of Nucleic Acids, then reiterating the steps of binding, partitioning, dissociating and amplifying through as many cycles as desired to yield highly specific, high affinity Nucleic Acid Ligands to the Target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned, describes the use of SELEX in conjunction with gel electrophoresis to select Nucleic Acid molecules with specific structural characteristics, such as bent DNA (see, U.S. Pat. No. 5,707,796). U.S. patent application Ser. No. 08/123,935, filed Sep. 17, 1993, entitled "Photoselection of Nucleic Acid Ligands" now abandoned, describes a SELEX based method for selecting Nucleic Acid Ligands containing photoreactive groups capable of binding and/or photocrosslinking to and/or photoinactivating a Target molecule. U.S. patent application Ser. No. 08/134,028, filed Oct. 7, 1993, entitled "High-Affinity Nucleic Acid Ligands That Discriminate Between Theophylline and Caffeine," now abandoned, describes a method for identifying highly specific Nucleic Acid Ligands able to discriminate between closely related molecules, termed Counter-SELEX (See, U.S. Pat. No. 5,580,737). U.S. patent application Ser. No. 08/143,564, filed Oct. 25, 1993, entitled "Systematic Evolution of Ligands by EXponential Enrichment: Solution SELEX," now abandoned, describes a SELEX-based method which achieves highly efficient partitioning between oligonucleotides having high and low affinity for a Target molecule (see, U.S. Pat. No. 5,567,588). U.S. patent application Ser. No. 07/964,624, filed Oct. 21, 1992, entitled "Methods of Producing Nucleic Acid Ligands" now U.S. Pat. No. 5,496,938, describes methods for obtaining improved Nucleic Acid Ligands after SELEX has been performed. U.S. patent application Ser. No. 08/400,440, filed Mar.8, 1995, entitled "Systematic Evolution of Ligands by EXponential Enrichment: Chemi-SELEX," now U.S. Pat. No. 6,705,337 describes methods for covalently linking a ligand to its Target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," now abandoned, that describes oligonucleotides containing nucleotide derivatives chemically modified at the 5- and 2'-positions of pyrimidines (see, U.S. Pat. No. 5,660,985). U.S. patent application Ser. No. 08/134,028, supra, describes highly specific Nucleic Acid Ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,638,867 and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing Nucleic Acid Ligands to CD4. Nucleic acid ligand sequences are provided that are capable of binding specifically to CD4. In particular, 2'F RNA sequences are provided that are capable of binding specifically to CD4. Specifically included within the scope of this invention are the RNA ligand sequences shown in Table 2 (SEQ ID NOS:7–24). Also included within the scope of this invention are RNA ligands that may inhibit the function of CD4.

Further included in this invention is a method of identifying Nucleic Acid Ligands and Nucleic Acid Ligand sequences to CD4 comprising the steps of (a) preparing a Candidate Mixture of Nucleic Acids, (b) contacting the Candidate Mixture of Nucleic Acids with CD4, (c) partitioning between members of said Candidate Mixture on the basis of affinity to CD4, and (d) amplifying the selected molecules to yield a mixture of Nucleic Acids enriched for Nucleic Acid sequences with a relatively higher affinity for binding to CD4.

More specifically, the present invention includes the RNA ligands to CD4, identified according to the above-described method, including those ligands shown in Table 2 (SEQ ID NOS: 7–24). Also included are RNA ligands to CD4 that are substantially homologous to any of the given ligands and that have substantially the same ability to bind CD4 and inhibit the function of CD4. Further included in this invention are Nucleic Acid Ligands to CD4 that have substantially the same structural form as the ligands presented herein and that have substantially the same ability to bind said CD4.

The present invention also includes modified nucleotide sequences based on the RNA ligands identified herein and mixtures of the same.

DETAILED DESCRIPTION OF THE INVENTION

Figure 1:
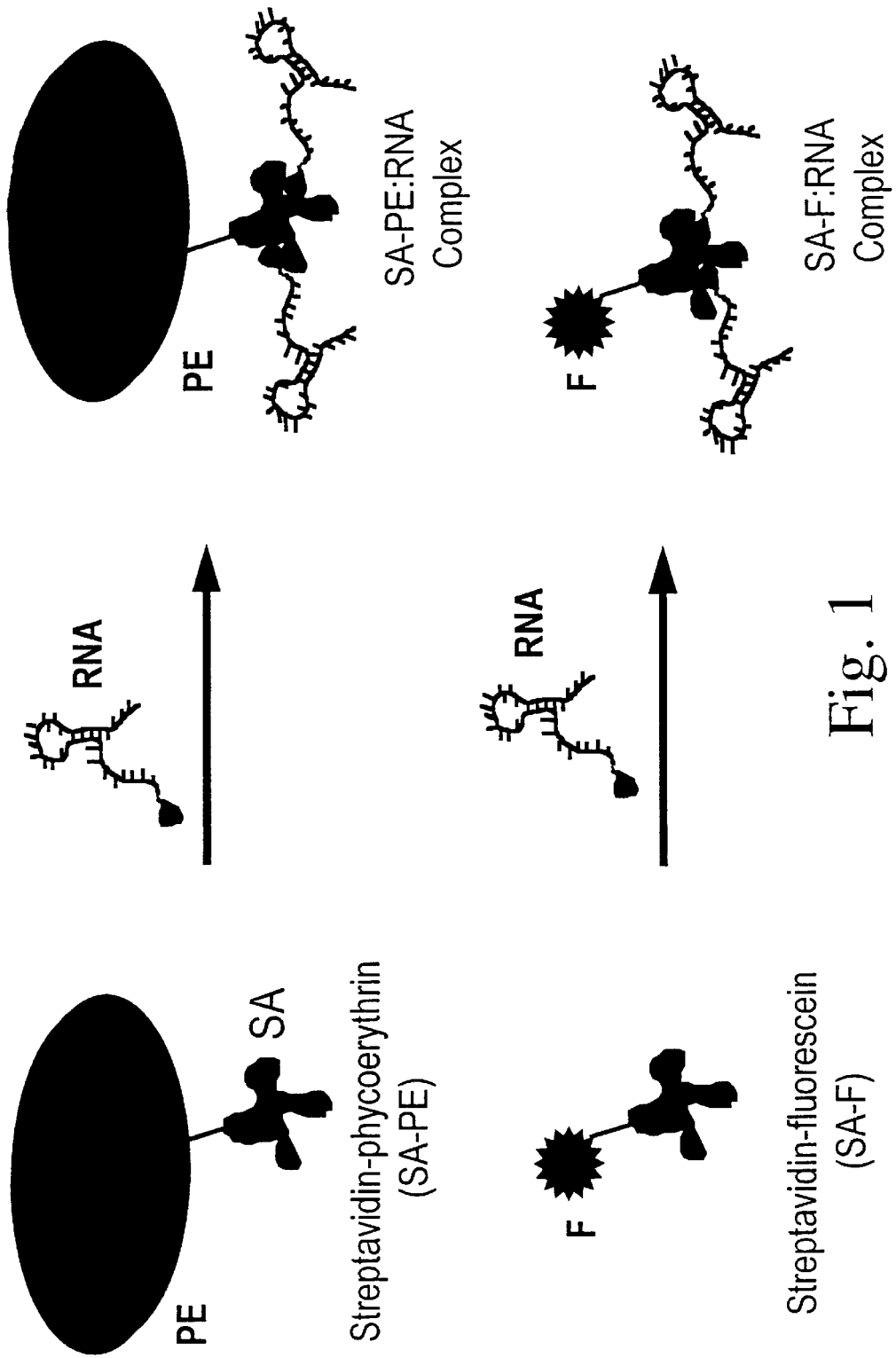
FIG. 1 depicts the reactions whereby RNA is conjugated to phycoerythrin through biotin-streptavidin interaction.

DEFINITIONS:

"Nucleic Acid Ligand" as used herein is a non-naturally occurring Nucleic Acid having a desirable action on a Target. A desirable action includes, but is not limited to, binding of the Target, catalytically changing the Target, reacting with the Target in a way which modifies/alters the Target or the functional activity of the Target, covalently attaching to the Target as in a suicide inhibitor, facilitating the reaction between the Target and another molecule. In the preferred embodiment, the action is specific binding affinity for a Target molecule, such Target molecule being a three dimensional chemical structure other than a polynucleotide that binds to the Nucleic Acid Ligand through a mechanism which predominantly depends on Watson/Crick base pairing or triple helix binding, wherein the Nucleic Acid Ligand is not a Nucleic Acid having the known physiological function of being bound by the Target molecule. Nucleic Acid Ligands include Nucleic Acids that are identified from a Candidate Mixture of Nucleic Acids, said Nucleic Acid Ligand being a ligand of a given Target, by the method comprising: a) contacting the Candidate Mixture with the Target, wherein Nucleic Acids having an increased affinity to the Target relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids.

"Candidate Mixture" is a mixture of Nucleic Acids of differing sequence from which to select a desired ligand. The source of a Candidate Mixture can be from naturally-occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process.

"Nucleic Acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"SELEX" methodology involves the combination of selection of Nucleic Acid Ligands which interact with a Target in a desirable manner, for example binding to a protein, with amplification of those selected Nucleic Acids. Optional iterative cycling of the selection/amplification steps allows selection of one or a small number of Nucleic Acids which interact most strongly with the Target from a pool which contains a very large number of Nucleic Acids. Cycling of the selection/amplification procedure is continued until a selected goal is achieved. In the present invention, the SELEX methodology is employed to obtain Nucleic Acid Ligands to a glycoprotein, CD4.

The SELEX methodology is described in the SELEX Patent Applications.

"SELEX Target" or "Target" means any compound or molecule of interest for which a ligand is desired. A Target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the SELEX Target is a glycoprotein, CD4.

SELEX is described in U.S. patent application Ser. No. 07/536,428, entitled Systematic Evolution of Ligands by EXponential Enrichment, now abandoned; U.S. patent application Ser. No. 07/714,131, filed Jun. 10, 1991, entitled Nucleic Acid Ligands, now U.S. Pat. No. 5,475,096; U.S. patent application Ser. No. 07/931,473, filed Aug. 17, 1992, entitled Nucleic Acid Ligands, now U.S. Pat. No. 5,270,163, (see also PCT/US91/04078). These applications, each specifically incorporated herein by reference, are collectively called the SELEX Patent Applications.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-Target pairs between the Target and those Nucleic Acids having the strongest affinity for the Target.

3) The Nucleic Acids with the highest affinity for the Target are partitioned from those Nucleic Acids with lesser affinity to the Target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5–50%) are retained during partitioning.

4) Those Nucleic Acids selected during partitioning as having the relatively higher affinity to the Target are then amplified to create a new Candidate Mixture that is enriched in Nucleic Acids having a relatively higher affinity for the Target.

5) By repeating the partitioning and amplifying steps above, the newly formed Candidate Mixture contains fewer and fewer weakly binding sequences, and the average degree of affinity of the Nucleic Acids to the Target will generally increase. Taken to its extreme, the SELEX process will yield a Candidate Mixture containing one or a small number of unique Nucleic Acids representing those Nucleic Acids from the original Candidate Mixture having the highest affinity to the Target molecule.

The SELEX Patent Applications describe and elaborate on this process in great detail. Included are Targets that can be used in the process; methods for partitioning Nucleic Acids within a Candidate Mixture; and methods for amplifying partitioned Nucleic Acids to generate enriched Candidate Mixture. The SELEX Patent Applications also describe ligands obtained to a number of target species, including both protein Targets where the protein is and is not a Nucleic Acid binding protein.

The Nucleic Acid Ligands to CD4 can be complexed with a lipophilic compound (e.g., cholesterol) or attached to or encapsulated in a complex comprised of lipophilic components (e.g., a liposome). U.S. patent application No. 08/434,465, filed May 4, 1995, entitled "Nucleic Acid Ligand Complexes," which is incorporated in its entirety herein, describes a method for preparing a therapeutic or diagnostic complex comprised of a Nucleic Acid Ligand and a lipophilic compound or a non-immunogenic, high molecular weight compound.

The methods described herein and the Nucleic Acid Ligands identified by such methods are useful for both therapeutic and diagnostic purposes. Therapeutic uses include the treatment or prevention of diseases or medical conditions in human patients, specifically CD4-mediated diseases. Diagnostic utilization may include both in vivo or in vitro diagnostic applications. The SELEX method generally, and the specific adaptations of the SELEX method taught and claimed herein specifically, are particularly suited for diagnostic applications. SELEX identifies Nucleic Acid Ligands that are able to bind targets with high affinity and with surprising specificity. These characteristics are, of course, the desired properties one skilled in the art would seek in a diagnostic ligand.

The Nucleic Acid Ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any Nucleic Acid Ligand by procedures known in the art to incorporate a labeling tag in order to track the presence of such ligand. Such a tag could be used in a number of diagnostic procedures. The Nucleic Acid Ligands to CD4 described herein may specifically be used for identification of the CD4 protein.

The ligands described herein are particularly suited for use in flow cytometry. U.S. patent application No. 08/479,729, which is herein incorporated by reference in its entirety, discloses the use of Nucleic Acid Ligands in flow cytometry. Flow cytometry, the measurement of cells in a moving liquid stream, is well established as a valuable analytical tool in research laboratories and clinical setting. Flow cytometry is unique, as compared to other diagnostic techniques, in its capability to perform simultaneous multiparameter analysis and to separate (or sort) unique cell populations from heterogeneous mixtures. The Nucleic Acid Ligands of the present invention can be used in flow cytometry to detect cells or particles containing the CD4 protein.

SELEX provides high affinity ligands of a target molecule. This represents a singular achievement that is unprecedented in the field of Nucleic Acids research. The present invention applies the SELEX procedure to the specific target of CD4. In the Example section below, the experimental parameters used to isolate and identify the Nucleic Acid Ligands to CD4 are described.

In order to produce Nucleic Acids desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand have the highest possible affinity to the target.

In co-pending and commonly assigned U.S. patent application Ser. No. 07/964,624, filed Oct. 21, 1992, methods are described for obtaining improved Nucleic Acid Ligands after SELEX has been performed (now U.S. Pat. No. 5,496,938). This patent, entitled Methods of Producing Nucleic Acid Ligands, is specifically incorporated herein by reference.

In the present invention, a SELEX experiment was performed in order to identify RNA with specific high affinity for CD4 from a degenerate library containing 40 random positions (40 N) (Example 1). This invention includes the specific RNA ligands to CD4 shown in Table 2 (SEQ ID NOS: 7–24), identified by the method described in Example 1. Specifically included within the scope of this invention are Nucleic Acid Ligands to CD4 identified by the SELEX method where CD4 is attached to the surface of a bead. The scope of the ligands covered by this invention extends to all Nucleic Acid Ligands of CD4, modified and unmodified, identified according to the SELEX procedure. More specifically, this invention includes Nucleic Acid sequences that are substantially homologous to the ligands shown in Table 2 (SEQ ID NOS 7–24). By substantially homologous it is meant a degree of primary sequence homology in excess of 70%, most preferably in excess of 80%. A review of the sequence homologies of the ligands of CD4 shown in Table 2 (SEQ ID NOS: 7–24) shows that sequences with little or no primary homology may have substantially the same ability to bind CD4. For these reasons, this invention also includes Nucleic Acid Ligands that have substantially the same structure and ability to bind CD4 as the Nucleic Acid Ligands shown in Table 2 (SEQ ID NOS 7–24). Substantially the same structure includes all nucleic acid ligands having the common structural elements shown in Table 2 that lead to the affinity to CD4. Substantially the same ability to bind CD4 means that the affinity is within one or two orders of magnitude of the affinity of the ligands described herein. It is well within the skill of those of ordinary skill in the art to determine whether a given sequence— substantially homologous to those specifically described herein—has substantially the same ability to bind CD4.

One potential problem encountered in the therapeutic and in vivo diagnostic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the Nucleic Acid Ligand can be made to increase the in vivo stability of the Nucleic Acid Ligand or to enhance or to mediate the delivery of the Nucleic Acid Ligand. See, e.g., U.S. patent application Ser. No. 08/117,991, filed Sep. 9, 1993, entitled High Affinity Nucleic Acid Ligands Containing Modified Nucleotides, which is specifically incorporated herein by reference. Modifications of the Nucleic Acid Ligands contemplated in this invention include, but are not limited to, those which provide other chemical groups that incorporate additional charge, polarizability, hydrophobicity, hydrogen bonding, electrostatic interaction, and fluxionality to the Nucleic Acid Ligand bases or to the Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

The modifications can be pre- or post-SELEX modifications. Pre-SELEX modifications yield Nucleic Acid Ligands with both specificity for their SELEX Target and improved in vivo stability. Post-SELEX modifications made to 2'-OH Nucleic Acid Ligands can result in improved in vivo stability without adversely affecting the binding capacity of the Nucleic Acid Ligand.

Other modifications are known to one of ordinary skill in the art. Such modifications may be made post-SELEX (modification of previously identified unmodified ligands) or by incorporation into the SELEX process.

As described above, because of their ability to selectively bind CD4, the Nucleic Acid Ligands to CD4 described herein are useful as pharmaceuticals. This invention, therefore, also includes a method for treating CD4-mediated diseases by administration of a Nucleic Acid Ligand capable of binding to CD4.

Therapeutic compositions of the Nucleic Acid Ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing Nucleic Acid Ligands for systemic delivery may be via subcutaneous, intramuscular, intravenous, intranasal or vaginal or rectal suppository.

In the Examples that follow, the use of SELEX methodology to identify high affinity RNA ligands to CD4 is described.

The following Examples are provided to explain and illustrate the present invention and are not intended to be limiting of the invention. Example 1 describes the various materials and experimental procedures used in Examples 2 and 3. Example 2 describes the conjugation of fluorescein and phycoerythrin to RNAs in the evolved pool, the binding of the enriched pool to CD4 beads, the region of CD4 to which RNAs in the evolved pool bind, and the binding of enriched pool RNA to CD4 expressed on cells. Example 3 describes the RNA ligands to CD4, the region of CD4 to which specific RNA ligands bind, and the binding of RNA ligands to CD4+ cells.

EXAMPLE 1

EXPERIMENTAL PROCEDURES

Materials

The full-length extracellular domain of human CD4 (amino acids 1–370) produced in a mammalian (Chinese hamster ovary) expression system was purchased from Dupont NEN (Boston, Mass.) as a 1 mg/mL solution in 350 mM NaCl, 50 mM MES (pH 6.0), and stored at −70° C. until use. Polymethylmethacrylate (PMMA) beads derivatized with amino functional groups on the surface was bought from Bangs Laboratories (Carmel, Ind.). Polystyrene beads (3.2 μm in diameter) were from IDEXX Laboratories (Westbrook, Me.). Streptavidin, iodoacetamido LC biotin and 5-iodoacetamido fluorescein were bought from Pierce Chemical company (Rockford, Ill.). Guanosine-5'-O-(2-thiodiphosphate) (GDP-β-S) was purchased from Calbiochem (La Jolla, Calif.). Streptavidin (SA) conjugated to phycoerythrin (PE) was obtained from Becton Dickinson. Deoxyoligonucleotides were synthesized by standard cyanoethyl phosphoramidite chemistry and purified by denaturing polyacrylamide gel electrophoresis to size homogeneity before use. B6 and BW5147 cells were obtained from Becton Dickinson.

CD4 attached to streptavidin beads

Polymethylmethacrylate amino beads (6.1 µm in diameter) were washed sequentially with ten volumes of PBS containing 0.1% sodium azide (1X), with three volumes of PBS containing 0.1% sodium dodecyl sulfate (2X) and with PBS (2X). The washed beads were then suspended in PBS containing 1.5 mM NHS-LC-biotin (from Pierce) at 3% (w/v), and incubated with mixing for one hour at room temperature. The beads were then washed twice with three volumes of PBS, and subsequently, suspended and stored overnight in PBS containing 0.1% sodium azide and 2% nonfat dry milk.

The beads were then suspended in PBS at 2.5% (w/v) and mixed with streptavidin (0.4 mg/mL) for two hours at room temperature, and subsequently, washed five times with six volumes of PBS containing 0.1% sodium azide and 0.5% BSA. The beads were finally stored as a 2.5% (w/v) suspension in this buffer at 4° C.

The biotinylation on CD4 was performed by incubating CD4 in PBS (pH 7.4) at 1 mg/mL with 0.1 mM NHS-LC-Biotin for two hours at room temperature. Unreacted biotin was removed by passing the reaction mixture through a Sephadex G-50 column. The extent of biotinylation on CD4 was assayed by binding to polystyrene beads coated with an anti-CD4 antibody (Leu3a) and staining with FITC-labeled streptavidin as compared with staining with an appropriate FITC-labeled second anti-CD4 antibody (e.g., FITC-L120).

CD4 on L200 beads

Polystyrene beads (3.3. µm in diameter) were washed with 50 mM MES buffer (pH 6.0) and suspended at 0.5% (w/v) in the same buffer. The anti-CD4 monoclonal antibody (clone L200) was added to 0.5 µg/cm$^2$ of bead surface area and incubated for 30 min. at room temperature. The beads were then washed twice with two volumes of PBS containing 0.5% BSA and stored in this buffer at a bead concentration of about 3×10$^8$/mL.

Immediately prior to use, 0.6 µg of CD4 suspended in PBS, 0.1% sodium azide and 0.5% BSA was incubated with 10 µL of L200 beads (3.2×10$^6$ beads) at room temperature for 1 hr with gentle mixing. Unbound CD4 was removed by washing the beads two times with 200 µL of a buffer consisting of PBS, 0.1% sodium azide and 0.5% BSA.

THE SELEX PROCESS

The starting random sequence RNA pool shown in Table 1 (SEQ ID NO: 2) was obtained by in vitro transcription of the corresponding synthetic DNA template (SEQ ID NO: 1) that was gel-purified (1 nmole) and subjected to four rounds of PCR (in 1 mL reaction volume). The PCR products (1 nmole) were transcribed in vitro by T7 RNA polymerase (1000 U) in 2 mL reaction consisting of 3 mM each of 2'-F-CTP and 2'-F-UTP, 1 mM each of ATP and GTP, 50 µCi of a-$^{32}$P-ATP, 40 mM Tris-HCl (pH 8.0), 12 mM MgCl$_2$, 1 mM Spermidine, 5 mM DTT, 0.002% Triton X-100 and 4% polyethelene glycol (w/v) for 10–12 hr at room temperature. The template DNA was digested with RNase-free DNAse I treatment. The full-length transcription products were purified on 8% denaturing polyacrylamide gels to ensure size homogeneity. In subsequent rounds of selections, in vitro transcription reactions were carried out in either 500 or 200 µL reaction volume with 100–400 pmoles of template DNA with 100–200 U of the polymerase.

In the initial round of selection, the random sequence RNA pool (2 nmoles) suspended in 1 mL of the binding buffer (standard PBS containing 2 mM MgCl$_2$) was heated to 80° C. for 3 min. and chilled on ice before being transferred to room temperature. Once equilibrated at room temperature, 20 µL of SA-CD4 beads were added to the RNA suspension, incubated at room temperature for 15 min. with gentle mixing and beads were recovered by centrifugation in a picofuge for 1 min. RNA molecules that were trapped between beads were removed by a one time wash with 100 µL of the binding buffer. The bead retained RNA was recovered by extracting with 1:2 (v/v) mixture of neutralized phenol:fresh 7M urea. Beads were back-extracted once with phenol/urea mixture, and the combined aqueous phases were ethanol precipitated in the presence of 5 µg of tRNA. The recovered RNA was reverse transcribed by avian myeloblastosis virus reverse transcriptase (Life Sciences) to obtain cDNA in a 50 µL reaction consisting of 50 mM Tris-HCl (pH 8.3), 60 mM NaCl, 6 mM Mg(OAc)2, 10 mM DTT, 0.4 mM dNTPs, 5 U of the enzyme and 50 pmoles of the 3'-primer (Table 1; SEQ ID NO: 4) at 48° C. for 45 min. The cDNA was amplified by PCR with the 5' and the 3' primers (primer set I; Table 1; SEQ ID NOS: 3–4), and the resulting DNA template was transcribed in vitro to obtain RNA for the next round of selection.

In subsequent rounds, the enriched RNA pools were exposed to 50 µL of the same beads lacking CD4 (control beads) to remove sequences that bind to sites on both CD4 and beads. In addition, during the course of selection, wash volumes were gradually increased from 50 µL to 1000 µL to effectively remove molecules with low affinity interactions.

The selection was performed with SA-CD4 beads up to six rounds and switched over to L200-CD4 beads to eliminate the undesirable selection of RNA that binds to the streptavidin beads. The selection on L200 beads was continued up to 15 rounds where the enriched pool was subjected to cloning and sequencing. To further increase the stringency of the selection of RNA that binds CD4 with high affinity, rounds 12–15 were carried out with low density L-200 beads on which the number of CD4 molecules per bead was approximately decreased by ten-fold.

The cDNA derived from the 15th round of selection was amplified by PCR with primer set 2 (Table 1; SEQ ID NOS: 5–6) to incorporate BamHI and ECoRI restriction site at the termini of the resulting duplex DNA. This DNA was gel purified and digested with BamHI and ECoRI and cloned into plasmid pUC 18 vector that has been previously digested with the same enzymes. Clones were sequenced by standard dideoxy sequencing technique (Sequenase kit from USB).

Preparation of fluoresceinated and biotinylated RNA

To prepare RNA derivatized with fluorescein or biotin, in vitro transcriptions were carried out in a reaction mixture containing a 10-fold excess of GDP-β-S (from Calbiochem) over GTP. Under these conditions GDP-β-S is incorporated at the 5'-end of the transcript. About 1–2 nmoles of gel purified RNA transcripts were suspended in 100 µL of a buffer consisting of 50 mM ammonium bicarbonate (pH 8.0), 2 mM EDTA, 4 mM DTT. After 15 min. incubation at room temperature, 300 µL of 4 mM iodoacetyl LC biotin in dimethyl formamide was added, mixed, and the pH of the reaction mixture was adjusted to 7.5–8.0 with 2N NaOH. The reaction proceeded at room temperature for 8–10 hr, and biotinylated RNA was recovered from the solution by ethanol precipitation. The precipitate was washed twice with 70% ethanol, suspended in 200 µL of TE buffer (10 mM Tris-HCl, 0.1 mM EDTA, pH 8.0) and residual unreacted biotin was removed by passing the RNA suspension through a 30 K$_d$ molecular weight cutoff spin filter (Schleicher &

Schull). The filter-retained RNA was washed three times with 400 μL of TE buffer before recovery.

To derivatize with fluorescein, DTT-treated RNA (1–2 nmoles) suspended in 50 μL of a buffer consisting of 50 mM ammonium bicarbonate (pH 8.0), 2 mM EDTA, 10 mM DTT was incubated with 50 μL of 200 mM 5-iodoacetamido fluorescein in dimethyl formamide for 2–3 hr at room temperature. Post coupling processing of fluoresceinated RNA was as described for the biotinylation protocol.

Preparation of SA-PE:RNA conjugates

RNA labeled with biotin at the 5' end was mixed with phycoerythrin-labeled streptavidin at a 3:1 ratio of RNA to 1 SA-PE in PBS (pH 7.4) and incubated for 16 hr at 4° C. The mixture was then fractionated by size exclusion on a Superose 6 HR 10/30 column using a buffer consisting of 50 mM sodium phosphate, 150 mM NaCl, 2M urea and 0.1% $NaN_3$ (pH 7.2). Fractions containing 0.35 mL were collected at a flow rate of 0.2 mL/min. The fractions containing SA-PE:RNA conjugates were pooled. The stoichiometry of RNA and PE in complexes were calculated by measuring UV absorption of the complex at 260 nM (for RNA) and 565 nM (for PE). A solution of RNA with one absorption unit per mL was considered as 40 μg/mL. SA covalently attached to fluorescein (SA-F) was used to obtain SA-F:RNA complexes.

Flow cytometry analysis

All flow cytometric analyses were performed on a FAC-Scan™ model flow cytometer (Becton Dickinson Immunocytometry Systems, San Jose, Calif.). Binding of RNA or antibodies to CD4 presented on beads was analyzed by incubation of either 9× $10^4$ streptavidin beads or 2.5×$10^5$ L200 beads in 50 μL volume of PBS buffer containing 2 mM $MgCl_2$ and 1 mg/mL BSA for 20 min. at room temperature in dark. Beads were then washed with 2 mL of the same buffer, suspended in 0.5 mL of the buffer and subjected to flow cytometric analysis.

Binding of RNA (or antibodies) to cell surface CD4 was determined using the same procedure described for beads except that about 5×$10^4$ cells for B6 and BW5147 and about 1.2×$10^5$ PBMCs were used for a given experiment.

EXAMPLE 2

The enriched RNA pool

As the selection progressed, there was enhanced retention of radiolabeled RNA to L200 beads containing CD4, compared to the control L200 beads lacking CD4, suggesting the enrichment of RNA sequences binding to CD4. To further confirm the selection of RNA ligands that specifically bind to CD4, the enriched RNA pool (round 15) was labeled with fluorescein at the 5' end and CD4 presented on beads in flow cytometry. The strategy used for labeling transcriptionally-derived RNA with fluorescein is described in Example 1. The enriched pool was able to bind both types of beads (L200 and SA beads) when CD4 was present, but not to the control beads lacking CD4. The unselected random sequence pool shows very little binding to CD4 on either beads and is detectable only at high RNA concentrations. These results indicate that the enriched RNA pool does in fact bind to CD4 on beads.

Fluorophores such as phycoerythrin that are brighter than fluoresceins are advantageous in flow cytometry. To accommodate this need, a strategy was designed to conjugate RNA to phycoerythrin through biotin-streptavidin interaction (FIG. 1). In this approach, the RNA pool derivatized with biotin at the 5' end was complexed with streptavidin (SA) that was covalently linked to phycoerythrin (PE). By controlling the stoichiometry of the two species, complexes were obtained with between 2–3 RNA molecules per SA-PE molecule. This approach further allowed the determination of the affinity of RNA ligands in a multimeric (or bivalent) form. Measurements of optical density at 260 nM (absorption maximum of RNA) and 565 nM (absorption maximum of PE) permitted the calculation of the stoichiometry of the two species in various fractions of a sizing column.

The binding of biotinylated RNA pools (both unselected and selected) complexed with SA-PE to the two types of beads (i.e., L200 and streptavidin) was tested. The selected RNA pool binds both types of beads containing CD4, the result in accord with the binding of fluoresceinated RNA pool. The binding of SA-PE:RNA pool to bead coupled CD4 indicates that RNA molecules in a very large protein complex (about 300 $K_d$) retained the recognition ability. The unselected random sequence pool conjugated to SA-PE also shows a fair amount of binding to the beads. This binding is not saturable even at 80 nM, indicating the nonspecific nature of the interaction. This observation, along with the detectable binding of fluoresceinated pool to streptavidin beads but not to L200 beads suggests that RNA shows more nonspecific binding to streptavidin beads compared to L200 beads, possibly due to the presence of exposed amine groups on streptavidin beads.

Binding regions (or epitopes) of many monoclonal antibodies that bind CD4 have been characterized. (Truneh et al., (1991) *J Biol. Chem.* 266:5942–5948) A panel of such antibodies (i.e., L113, L117, L121, L34, L68, L69, L80, L82, L83, L88, and L92) was used to determine the approximate binding domain(s) of the enriched RNA pool on the CD4 molecule. In this experiment CD4 on SA beads or L200 beads were preincubated with 1 μg of an unlabeled antibody or a mixture of 8 antibodies (L34, L68, L69, L80, L82, L83, L88, and L92) for 10 minutes at room temperature prior to addition of fluoresceinated RNA to a final concentration of 100 nM. Antibodies that bind to the V4 region of CD4 (L 113, L121 & L120) completely blocked the binding of the selected RNA pool. Antibodies L117 (bind V2 and V4) and Leu3b (V1/V2 interface) showed minimum level of blocking. L216 that is known to interact with the V2 region exerted about 50% blockade of the RNA binding. Out of the antibodies that are known to bind the V1 region, Leu3a and L71 blocked the pool binding by about 50%, whereas L200 and L240 were not as effective as Leu3a and L71 in blocking the RNA binding. Overall, the data of the antibody blocking experiment suggest that the majority of the ligands in the selected pool interacts with CD4 at the V4 region that resides next to the cytoplasmic membrane. The ability of some of the antibodies that bind the V1 region and one antibody that binds the V2 region to block the pool binding by one half may indicate the presence of ligands binding to these two regions as well. Alternatively, the latter result could be due to the long range steric hindrance caused by these antibodies, preventing RNA to interact with the V4 region.

The observation of high-affinity binding of the enriched RNA pool to recombinant CD4 on beads prompted the investigation of the binding of RNA to CD4 expressed on cells. Mouse T-cell lines with and without human CD4 on their surface were stained with a monoclonal antibody LEU3A-fluorescein isothiocyanate (FITC) and the selected RNA pool labeled with fluorescein. Mouse T-cell line (BW5147), which lacks human CD4, and the same cell line transfected with human CD4 (B6) were incubated at room temperature for 20 minutes (50,000 cells in 50 μl final volume) in PBS, 2 mm MGCL2 and 0.1% BSA. Cells were washed with 2 ml of buffer and suspended in 0.5 ml of buffer for analysis. Strong binding of fluorosceinated antibody to CD4 (Leu3a-FITC) to B6 cells but not to BW4157 was observed. Analogous to the antibody to CD4, the fluorosceinated RNA pool that was selected on recombinant CD4 on beads binds specifically to B6 cells, but not to the control BW4157 cells lacking human CD4 on the surface.

The two mouse cell lines were also stained with the selected RNA pool conjugated to SA-PE ($RNA_{pool}5$:SA-PE). An antibody to CD4 (Leu3a) labeled with PE was used as a positive control. The staining of B6 cells with $RNA_{pool}5$:SA-PE was very similar to that of CD4(Leu3a)-PE. However, contrary to antibody staining, there was a low level of nonspecific staining on BW5147 with the RNA conjugate. Since RNA was conjugated to PE through streptavidin, it was investigated whether the background binding is due to SA-PE by staining the two cell types with SA-PE. SA-PE did not show nonspecific staining on these cells.

EXAMPLE 3

2'-F RNA ligands to CD4

The binding characteristics of RNA to CD4 beads was not significantly improved after the 15th round of selection. As a result, the 15th round pool was analyzed by molecular cloning and sequencing. The sequence complexity of the 15th round RNA pool is shown in Table 2. Sequences were grouped into four classes based on sequence similarity. Sequences in classes I–III that represent about 60% of the pool are different from those in class IV (not shown). Class IV represents a group of sequences that are highly rich in pyrimidines with little or no homology among one another (not shown). On the other hand, sequences in classes I, II and III are highly homologous within a class. Members in these three classes differ among each other by minor base variations, probably caused by random mutagenesis in PCR. There is a significant degree of complementarity in base pairing within the variable regions of sequences of classes I–III, suggesting the potential for the formation of snap-back stem-loop structures (See overlining in Table 2—► indicates complementary regions; and ● a base that does not pair in the helical region.

In order to determine binding affinities of individual ligands, complexes of RNA:SA-PE were prepared for several representative ligands from each class. Fluorescence intensities of CD4 beads (L200 beads) stained with RNA:SA-PE complexes were measured by flow cytometry and those values were plotted as a function of the complex concentration to calculate the equilibrium dissociation constant ($K_d$s). In calculating the $K_d$s, the mean fluorescence of beads was plotted against the log concentration of RNA:SA-PE complex. The $K_d$s of four representative ligands from classes I–III were obtained and are shown in Table 3. Table 3 indicates the stoichiometries of RNA:SA-PE complexes and the calculated $K_d$ values of several ligands. Overall, the $K_d$ values that are in subnanomolar range indicate high affinity binding of RNA to CD4. In all cases there was more than one RNA molecule per complex, and hence the $K_d$ values in Table 3 reflect the interaction of RNA sequences in their multimeric form with CD4 on beads, conditions at which avidity is contributing to bimolecular interaction. Thus, the $K_d$ values of monomeric RNA sequences binding to CD4 in solution are expected to be higher than the calculated $K_d$s listed in Table 3. The binding analysis of individual ligands indicates that the sequences with high affinity binding to CD4 belong to classes I–III, whereas the sequences of class IV do not bind to CD4. Within classes I and II highly conserved sequence regions can be identified (Table 2) suggesting the possibility of the emergence of members of these two classes from a common progenitor sequence. On the other hand, however, class III sequences appear to be unrelated to those in classes I and II.

Since RNA ligands with high-affinity binding to CD4 were grouped into three classes, it was desirable to know whether ligands in different classes bind to different sites on CD4. This was investigated by antibody blocking experiment as described above for the selected RNA pool. The results are summarized in Table 4. The binding of representative ligands belonging to class I and III to CD4 on beads was completely abolished by antibody L120 that binds CD4 at V4 region, and partially blocked by antibody L117 that recognize V4 and V2 domains. These results are consistent with that observed for the RNA pool. However, the binding of ligand 21 belonging to class II was not completely blocked by antibody L120 (only about 80% was blocked), suggesting that ligands of this class may have a different binding site (yet overlapping with those of classes I and II) on CD4.

Figure 2A:
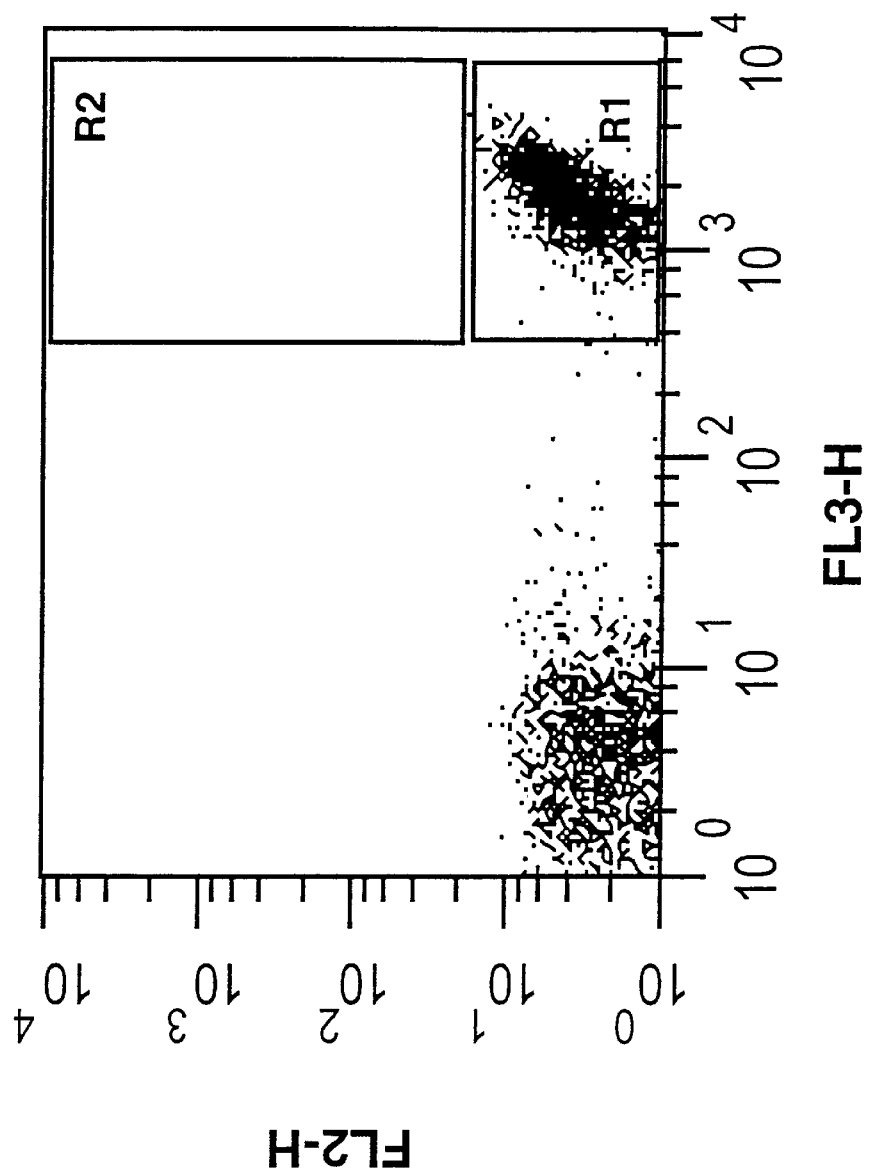
FIGS. 2a–2c depict the results of staining of T lymphocytes in human peripheral blood mononuclear cells with a monoclonal antibody to CD4 or an RNA ligand.
Figure 2B:
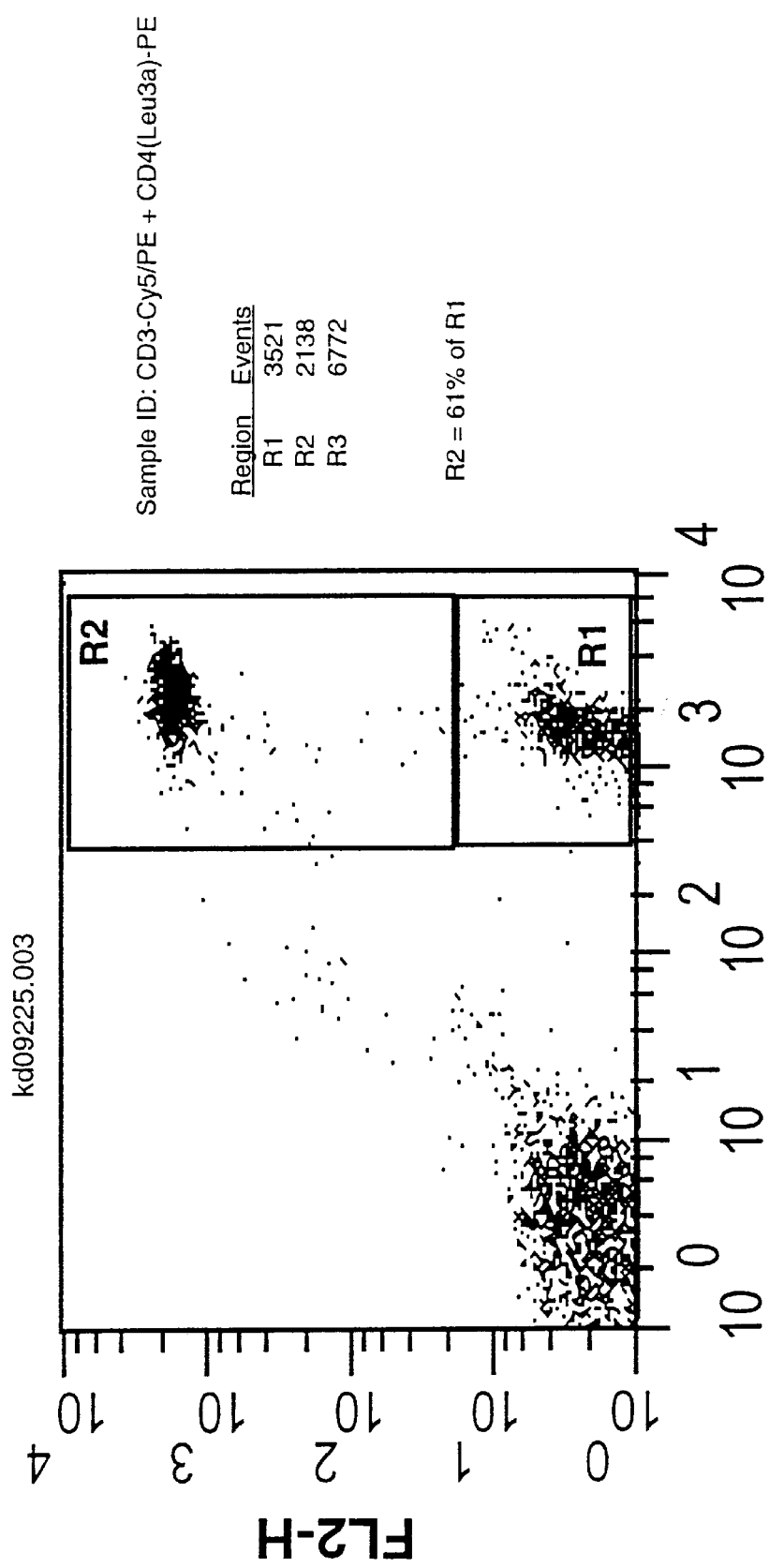
Figure 2C:
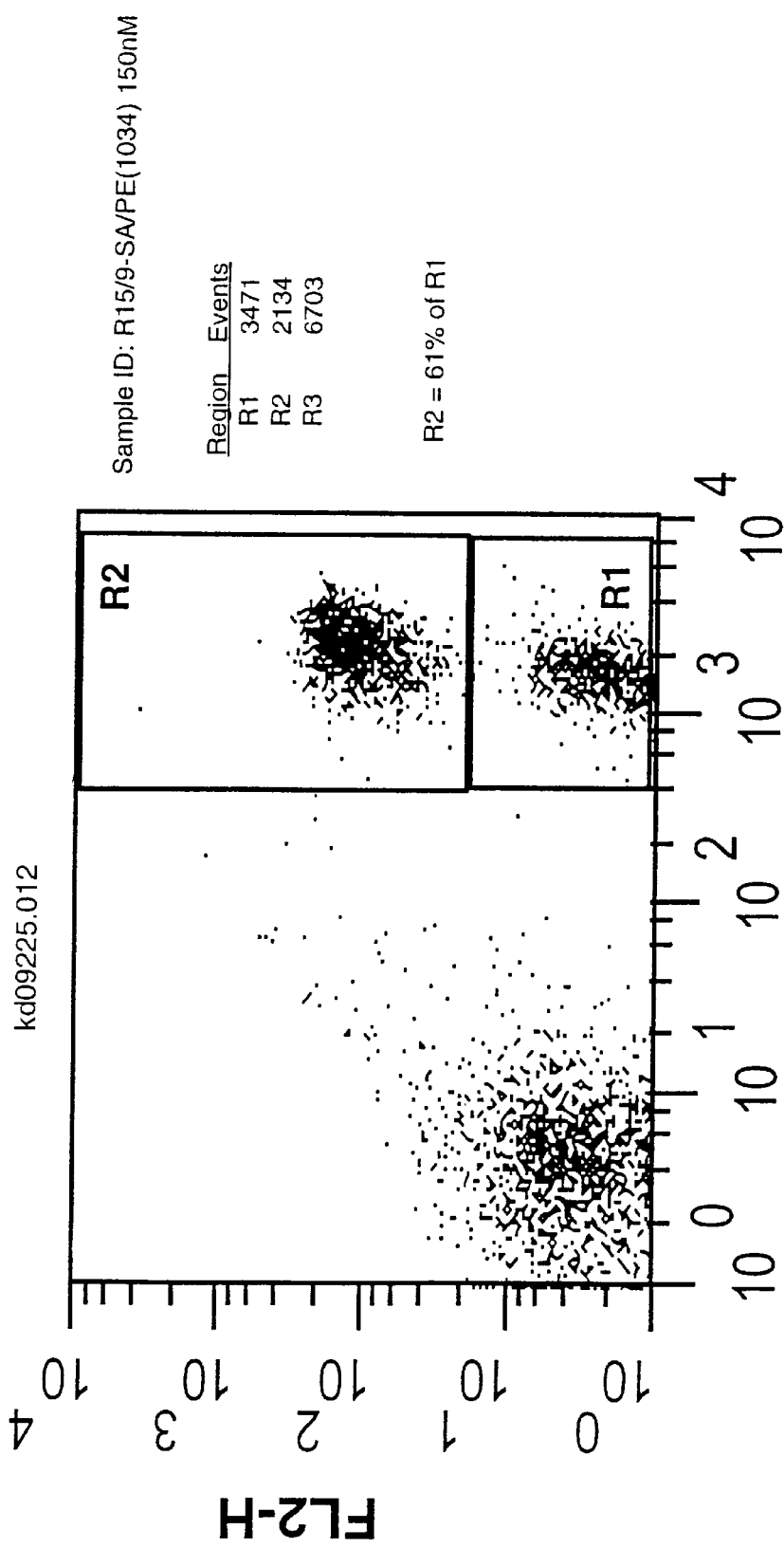

The positive staining observed with the selected RNA pool on B6 cells indicates that oligonucleotides selected on a recombinant protein can in fact recognize the same protein expressed on cells. To investigate specific binding of an RNA ligand to $CD4^+$ cells in a heterogeneous mixture of cells, T lymphocytes in human peripheral blood mononuclear cells (PBMC) preparation were stained with either a monoclonal antibody to CD4 (Leu 3a)-PE or an RNA ligand selected for CD4 binding (Ligand 9:SA-PE). PBMC's were incubated in a buffer consisting of PBS, 2 mM $MgCl2$ and 0.1% BSA with either two antibodies: CD3 (Leu4)-Cy5-PE and CD4 (Leu 31)-PE or with an antibody and RNA complex: CD3(Leu4)-Cy5-PE and Ligand 9:SA-PE for 15 minutes at room temperature. Cells were washed with 2 ml and suspended in 0.5 ml of the same buffer for analysis. In this experiment the antibody to CD3 stains all T cells ($CD3^+$). About 65% of $CD3^+$ T cells are $CD4^+$ T helper cells that should be stained either with an antibody to CD4 or with the selected RNA ligand. The results of this experiment are summarized in FIG. 2. Panel a of FIG. 2 shows the staining of PBMCs with the antibody to CD3, and the gate R2 represents the total T cell population in this sample. This T cell population splits into two subpopulations upon staining with antibody to CD4 (panel b; FIG. 2); $CD4^+$ cells are gated in R1. The calculated percentage of the $CD4^+$ T cells by antibody staining is 63. Staining pattern similar to that of panel b was obtained upon incubating with the RNA ligand (panel c; FIG. 2). The calculated percentage of the $CD4^+$ T cells by RNA staining is also 63, suggesting that the RNA ligands specifically identify CD4 on cell surface.

An antibody that recognizes CD4 at the V1 domain (for example, Leu3a) did not interfere drastically with the binding of RNA ligand 12 (Table 4), indicating that Leu3a and RNA ligand 12 can have simultaneous binding to CD4. This feature the investigation of co-staining of PBMCs with Leu3a and RNA ligand 12. In this experiment, PBMCs were stained with three different probes labeled with three different fluorophores; RNA ligand 12 complexed with SA-PE (Ligand 12:SA-PE), an antibody to CD4 (Leu3a labeled with FITC) and an antibody to CD14 (LeuM3) labeled with peridinine chlorophyll-a protein (PerCP).

Co-staining patterns generated by the two CD4 probes indicate that all the cells stained with Leu3a are also stained with the RNA ligand, suggesting that these two probes are binding to a common target, namely CD4 on the cell surface.

References

Anderson, P., Blue, M. L. & Schlossman, S. F. (1988) *J. Immunology* 140, 1732–1737.

Alves, A. M., Holland, D., Edge, M. D. & Carr, F. J. (1988) *Nucleic Acids Res.* 16, Balzarini, J., Mitsuya, M., DeClercq, E. & Broder, S. (1986) *Int. J. Cancer* 37, 451–457.

Benjamin, R. J. & Waldmann, H. (1986) *Nature* 320, 449–451.

Bendelac, A., Carnaud, C., Boitard, C. & Bach, J. F. (1987) *J. Experimental Medicine* 166, 823–832.

Cosimi, A. B., Delmonico, F. L., Wright, J. K., Wee, S. L., Preffer, F. I., Bedel, M. & Cloven, R. B. (1991) *Transplantation Proceedings* 23, 501–503.

Cobbold, S. P., Jayaswiya, A., Nash, A., Prospero, T. D. & Waldmann, H. (1984) *Nature* 312, 548–551.

Charlton, B. & Mandel, T. (1988) *Diabetes* 37, 1108–1112.

Christadoss, P. & Dauphinee, M. J. (1986) *J. Immunology* 136, 2437–2440.

Cosimi, A. B., Delmonico, F. L. & Wright, J. K. (1990) *Surgery* 108, 406–408.

Dalgleish, A. G., Beverley, P. C. L., Clapham, P. R., Crawford, D. H., Greaves, M. F. & Weiss, R. A. (1984) *Nature* 312, 767–772.

DeWolf, F., Roos, M., Lange, J. M. A. et al., (1988) *AIDS Res. Hum. Retroviruses* 4, 433–440.

Dhiver, C., Olive, D., Rousseau, S., Tamalet, C., Lopez, M., Galindo, J. -R., Mourens, M., Hirn, M., Gastand, J. A. & Mawas, C. (1989) *J. AIDS* 3, 835–842.

Doyle, C. & Strominger, J. L. (1987) *Nature* 330, 256–259.

Emmrich, F., Rieber, P., Kurrle, R. & Eichmann, K. (1986) *Eur. J. Immunol.* 18, 645–648.

Emmrich, F., Kanz, L. & Eichmann, K. (1987) *Eur. J. Immunol.* 17, 529–534.

Ghosh, S. S., Kao, P. M. & Kwoh, D. Y. (1989) *Anal. Biochem.* 178, 43–51.

Goronzy, J., Weyand, C. M. & Fathman, C. G. (1986) *J. Experimental Medicine* 164, 911–925.

Haskins, K., Portas, M., Bergman, B., Lafferty, K. & Bradley, B. (1989) *Proc. Natl. Acad. Sci. USA* 86, 8000–8004.

Hayward, A. R., Cobbold, S. P., Waldmann, H., Cooke, A. & Simpson, E. (1988) *J Autoimmunity* 1, 91–96.

Herzog, C., Walker, C., Pichloer, W., Aeschliman, A. & Wassmer, P. (1987) *Lancet* 333, 1461–1462.

Hom, J. T., Butler, L. D., Riedl, P. E. & Bendele, A. M. (1988) *Eur. J. Immunology* 18, 881–888.

Jabolinski, E., Moomaw, E. W., Tullis, R. H. & Ruth, J. L. (1986) *Nucleic Acids Res.* 14, 6115–6128.

Jonker, M., Neuhaus, P., Zurcher, C., Fucello, A. & Goldstein, G. (1985) *Transplantation* 39, 247–253.

Jonker, M., Nooij, F. J. M. and Stembof, G. (1987) *Transplant. Proceed* 19, 4308–4314.

Kelley, V. E., Gaulton, G. N. & Strom, T. B. (1987) *J. Immunology* 138, 2771–2775.

Koike, T., Itoh, Y., Ishii, T., Ito, I., Takabayashi, K., Muruyama, N., Tomoika, H. & Yoshida, S. (1987) *Diabetes* 39, 539–541.

Kupfer, A., Singer, S. J., Janeway, C. A. & Swain, S. L. (1987) *Proc. Natl. Acad. Sci USA* 84, 5888–5892.

Kwong, P. D., Ryu, S. -E., Hendrickson, W., Axel, R., Sweet, R., Folena-Wasserman, G., Hensley, P. & Sweet, R. (1990) *Proc. Natl. Acad. Sci. USA* 87, 6423–6427.

Lederman, S., Gulick, R. & Chess, L. (1989) *J. Immunol.* 143, 1149–1154.

Littman, D. R. (1987) *Ann. Rev. Immunol.* 5, 561–584.

Maddon, P. J., Littman, D. R., Godfrey, M., Maddon, D. E., Chess, L. & Axel, R. (1985) *Cell* 42, 93–104.

Maddon, D. R., Dagleish, A. G., McDougal, J. S., Clapham, P. R., Weiss, R. A. & Axel, R. (1986) *Cell* 47, 333

Maddon, P. J., Molineaux, S. M., Maddon, D. E., Zimmerman, K. A., Godfrey, M., Alt, F. W.. Chess, L. & Axel, R. (1987) *Proc. Natl. Acad. Sci. USA* 84, 9155–9159.

Madsen, J. C., Peugh, W. N., Wood, K. J. & Morris, P. J. (1987) *Transplantation* 44, 849–851.

Maino V. C., Suni, M. A. & Ruitenberg, J. J. (1995) *Cytometry* 20, 127–133.

Matsukura, M., Zon, G., Shinozuka, K., Robert-Guroff, M., Shimada, T., Stein, C. A., Mitsuya, H., Wong-Staal, F., Cohen, J. S. & Broder, S. (1989) *Proc. Natl. Acad. Sci. USA* 86, 4244–4248.

Morel, P., Vincent, C., Cordier, G., Panaye, G., Carosella, E. & Revillard, J. P. (1990) *Clinical Immunology & Immunopathology* 56, 311–322.

National Institute of Health (1990) *JAMA* 263, 1606–1609

Powelson, J. A., Knowles, R. W., Delmonico, F. L., Kawai, T., Mourad, G., Preffer, F. I., Colvin, R. B. & Cosimi, A. B. (1994) *Transplantation* 57, 788–793.

Quin, S., Wise, M., Cobbold, S. P., Leong, L., Kong, Y. -C., Parnes, J. R. & Waldmann, H. (1990) *Eur. J. Immunol.* 20, 2737–2745.

Sabilinski, T., Hancock, W. H., Tinley, N. L. & Kupiec-Weglinski, J. W. (1991) *Transplantation* 52, 579–589.

Saizawa, K., Rojo, J., & Janeway, C. A. (1987) *Nature* 328, 260–263.

Shizuru, J. A., Seydel, K. B., Flavin, T. F., Wu, A. P., Kong, C. C., Granthoyt, E., Fujimoto, N., Billingham, M. E., Starnes, V. A. & Fathman, C. G. (1990) *Transplantation* 50, 366–373.

Stein, C. A., Neckers, L., Nair, B., Mumbauer, S., Hoke, G. & Pal, R. (1991) *J. AIDS* 4, 686–693.

Stein, C. A., Cleary, A., Yakubov, L. & Lederman, S. (1993) *Antisense Res. Dev.* 3, 19–31.

Urdea, M. S., Warner, B. D., Running, J. A., Stempien, M., Clyne, J. & Horn, T. (1988) *Nucleic Acids Res.* 16, 4937–4956.

van der Lubbe, P. A., Reiter, C., Riethmuller, G., Sanders, M. E. & Breedveld, F. C. (1991) *Arthritis and Rheumatism* 34, S89.

Waldor, M., Syiram, K. S., Hardy, R., Herzenberg, L. A., Herzenberg, L., Lanier, L., Lim, M. and Steinman, L. (1985) *Science,* 227, 415–417.

Wang, J., Yan, Y., Garret, T. P. J., Liu, J., Rodgers, D. W., Garlick, R. L., Tarr, G. E., Husain, Y., Reinherz, E. L. & Harrison, S. C. (1990) *Nature* 348, 411–418.

Wofsy, D. & Seaman, W. E. (1985) *J. Experimental Medicine* 161, 378–391.

Wofsy, D. & Seaman, W. E. (1987) *J. Immunology* 138, 3247–3253.

Weaver, J., Gergely, P., Pine, P., Patzer, E. & Aszalos, A. (1990) *AIDS Res. Hum. Reteroviruses* 6, 1125–1130.

Weaver, J., Pine, P., Anand, R., Bell, S. & Aszalos, A. (1992) *Antiviral Chem. & Chemother.* 3, 147–151.

Weyand, C. M., Goronzy, J., Swartztrauber, K. & Fathman, C. G. (1989) *Transplantation* 47, 1039–1042.

Woodcock, J., Wofsy, D., Eriksson, E., Scott, J. H. & Seaman, W. E. (1986) *Transplantation* 42, 636–642.

TABLE 1

| SEQ ID NO. | |
|---|---|
| | Synthetic DNA template: |
| 1 | 5'-TAATACGACTCACTATAGGGAGACAAGAATAAACGCTCAA—[N]₄₀—TTCGACAGGAGGCTCACAACAGGC-3' |
| | Starting random sequence RNA pool: |
| 2 | 5'-GGGAGACAAGAAUAAACGCUCAA—[N]₄₀—UUCGACAGGAGGCUCACAACAGGC-3' |
| | Primer set I: |
| 3 | 5'-PRIMER I: 5'-TAATACGACTCACTATAGGGAGACAA-3' |
| 4 | 3'-PRIMER I: 5'-GCCTGTTGTGAGCCTCCTGTCGAA-3' |
| | Primer set II: |
| 5 | 5'-PRIMER II:<br>5'-CAG<u>AAGCTT</u>AATACGACTCACTATAGGGAGACAAGAATAAACGCTCAA-3'<br>      Hind III |
| 6 | 3'-PRIMER II:<br>5'-GACT<u>GGATCC</u>GCCTGTTGTGAGCCTCCTGTCGAA-3'<br>      Bam HI |

TABLE 2

| | SEQ ID NO. | CLONE NO. | NO. OF CLONES | Sequence |
|---|---|---|---|---|
| Class I | 7 | 2 | (9) | UGACGUCCUGAGAAUUGCGCAUUCCUCACACAGGAUCUU |
| | 8 | 9 | (2) | UGACGUCCUUAGAAUUGCGCAUUCCUCACACAGGAUCUU |
| | 9 | 59 | | UGACGUCCUGAGAAUUGCGCAUUCCUAACAUAGGAUCUC |
| | 10 | 65 | | UGACGUCCUAAGAAUUGCGCAUUCCUCACACAGGAUCUU |
| | 11 | 72 | | UGACGUCCUGAGAAUUGCGCAUUCCUCACACAGGAUCUU |
| | 12 | 16 | | UGACGUCCUAAGAAUUGCGCAUUCCUCACACAGGAUCUU |
| Class II | 13 | 12 | (13) | GUGACGUCCUGAUCGAUUGUGCAUUCGGUGUGACGAUCU |
| | 14 | 17 | | GUGACGUCCUGAUCGAUUGUGCAUUCGUUGUGACGAUCU |
| | 15 | 19 | | GUGACGUCCGGAUCGAUUGUGCAUUCGGGAUUACGAUCU |
| | 16 | 15 | | AUGACGUCCGGAUCGAUUGUGCAUUCGGGAUUACGAUCU |
| | 17 | 21 | | AUGACGUCCUGAUCGAUUGUGCAUUCGGGGUUACGAUCU |
| | 18 | 28 | | UUGACGUCCUGAUCGAUUGUGCAUUCGGUGUGACGAUCU |
| | 19 | 54 | | GUGACGUCCUGAUCGAUUGUGCAUUCGGGGUUACGAUCU |
| | 20 | 57 | | GUGACGUCCUGAUCGAUUGUGCAUUCGGGGUUACGAUCU |
| | 21 | 61 | | AUGACGCCCUGAUCGAUUGUGCAUUCGGGGUUACGAUCU |
| Class III | 22 | 7 | (3) | UGUGUCGUCCUGGUACGAUUUUGGUAUAUAACCGUGGCUU |
| | 23 | 8 | | UGUGUCGUCCUGGUACGAUUUUGGUAUAUAACCGCGGCUU |
| | 24 | 46 | | CGUGUCGUCCUGGUACGAUUUUGGUAUAUAACCGUGGCUU |

TABLE 3

| Ligand | Stoichiometry* | $K_d$** (complex) |
|---|---|---|
| 7 | 3.2 | 0.5 ± 0.05 |
| 9 | 3.3 | 0.9 ± 0.09 |
| 12 | 1.9 | 0.5 ± 0.07 |
| 21 | 2.9 | 0.4 ± 0.02 |
| Pool (15th Round) | 3.2 | 1.5 ± 0.08 |

*RNA molecules per SA:PE conjugate
**in nM

TABLE 4

| | % Blocking with Antibody | | | |
|---|---|---|---|---|
| Ligand | L117 | L120 | Leu3a | Leu3b |
| 9 | 60 | 99 | 35 | 35 |
| 21 | 57 | 81 | 23 | 17 |
| 7 | 66 | 99 | 35 | 35 |

We claim:

1. A purified and isolated non-naturally occurring nucleic acid ligand to CD4, wherein said ligand is an RNA selected from the group consisting of the sequences set forth in Table 2 (SEQ ID NOS:7–24).

* * * * *

SEQUENCE LISTING ( 1 ) GENERAL INFORMATION:

( i i i ) NUMBER OF SEQUENCES: 24

( 2 ) INFORMATION FOR SEQ ID NO: 1:

( i ) SEQUENCE CHARACTERISTICS:
  ( A ) LENGTH: 104 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO: 1:

```
TAATACGACT  CACTATAGGG  AGACAAGAAT  AAACGCTCAA  NNNNNNNNN        50
NNNNNNNNN  NNNNNNNNN  NNNNNNNNN  TTCGACAGGA  GGCTCACAAC         100
AGGC                                                            104
```

( 2 ) INFORMATION FOR SEQ ID NO: 2:

( i ) SEQUENCE CHARACTERISTICS:
  ( A ) LENGTH: 87 base pairs
  ( B ) TYPE: nucleic acid
  ( C ) STRANDEDNESS: single
  ( D ) TOPOLOGY: linear ( i i ) MOLECULE TYPE: RNA (genomic)

( x i ) SEQUENCE DESCRIPTION: SEQ ID NO: 2:

```
GGGAGACAAG  AAUAAACGCU  CAANNNNNN  NNNNNNNNN  NNNNNNNNN          50
NNNNNNNNN  NNNUUCGACA  GGAGGCUCAC  AACAGGC                       87
```

( 2 ) INFORMATION FOR SEQ ID NO: 3:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO: 3:

```
TAATACGACT  CACTATAGGG  AGACAA                                   26
```

( 2 ) INFORMATION FOR SEQ ID NO: 4:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO: 4:

```
GCCTGTTGTG  AGCCTCCTGT  CGAA                                     24
```

( 2 ) INFORMATION FOR SEQ ID NO: 5:

( i ) SEQUENCE CHARACTERISTICS:
  ( A ) LENGTH: 48 base pairs
  ( B ) TYPE: nucleic acid
  ( C ) STRANDEDNESS: single ( D ) TOPOLOGY: linear ( i i ) MOLECULE TYPE: DNA (genomic)

( x i ) SEQUENCE DESCRIPTION: SEQ ID NO: 5:

CAGAAGCTTA ATACGACTCA CTATAGGGAG ACAAGAATAA ACGCTCAA    48

( 2 ) INFORMATION FOR SEQ ID NO: 6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 6:

GACTGGATCC GCCTGTTGTG AGCCTCCTGT CGAA    34

( 2 ) INFORMATION FOR SEQ ID NO: 7:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 7:

GGGAGACAAG AAUAAACGCU CAAUGACGUC CUGAGAAUUG CGCAUUCCUC    50

ACACAGGAUC UUUUCGACAG GAGGCUCACA ACAGGC    86

( 2 ) INFORMATION FOR SEQ ID NO: 8:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 8:

GGGAGACAAG AAUAAACGCU CAAUGACGUC CUUAGAAUUG CGCAUUCCUC    50

ACACAGGAUC UUUUCGACAG GAGGCUCACA ACAGGC    86

( 2 ) INFORMATION FOR SEQ ID NO: 9:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 9:

GGGAGACAAG AAUAAACGCU CAAUGACGUC CUGAGAAUUG CGCAUUCCUA    50

ACAUAGGAUC UCUUCGACAG GAGGCUCACA ACAGGC    86

( 2 ) INFORMATION FOR SEQ ID NO: 10:

( i ) SEQUENCE CHARACTERISTICS:
        ( A ) LENGTH: 86 base pairs
        ( B ) TYPE: nucleic acid ( C ) STRANDEDNESS: single
            ( D ) TOPOLOGY: linear ( i i ) MOLECULE TYPE: RNA (genomic)

( x i ) SEQUENCE DESCRIPTION: SEQ ID NO: 10:

GGGAGACAAG AAUAAACGCU CAAUGACGUC CUAAGAAUUG CGCAUUCCUC         50

ACACAGGAUC UUUUCGACAG GAGGCUCACA ACAGGC         86

( 2 ) INFORMATION FOR SEQ ID NO: 11:

( i ) SEQUENCE CHARACTERISTICS:
            ( A ) LENGTH: 86 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO: 11:

GGGAGACAAG AAUAAACGCU CAAUGACGUC CUGAGAAUUG CGCAUUCCUC         50

ACACAGGAUC UUUUCGACAG GAGGCUCACA ACAGGC         86

( 2 ) INFORMATION FOR SEQ ID NO: 12:

( i ) SEQUENCE CHARACTERISTICS:
            ( A ) LENGTH: 86 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO: 12:

GGGAGACAAG AAUAAACGCU CAAUGACGUC CUAAGAAUUG CGCAUUCCUC         50

ACACAGGAUC UUUUCGACAG GAGGCUCACA ACAGGC         86

( 2 ) INFORMATION FOR SEQ ID NO: 13:

( i ) SEQUENCE CHARACTERISTICS:
            ( A ) LENGTH: 86 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO: 13:

GGGAGACAAG AAUAAACGCU CAAGUGACGU CCUGAUCGAU UGUGCAUUCG         50

GUGUGACGAU CUUUCGACAG GAGGCUCACA ACAGGC         86

( 2 ) INFORMATION FOR SEQ ID NO: 14:

( i ) SEQUENCE CHARACTERISTICS:
            ( A ) LENGTH: 86 base pairs
            ( B ) TYPE: nucleic acid
            ( C ) STRANDEDNESS: single
            ( D ) TOPOLOGY: linear ( i i ) MOLECULE TYPE: RNA (genomic)

( x i ) SEQUENCE DESCRIPTION: SEQ ID NO: 14:

GGGAGACAAG AAUAAACGCU CAAGUGACGU CCUGAUCGAU UGUGCAUUCG         50

UUGUGACGAU CUUUCGACAG GAGGCUCACA ACAGGC         86

( 2 ) INFORMATION FOR SEQ ID NO: 15:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 15:

```
GGGAGACAAG  AAUAAACGCU  CAAGUGACGU  CCGGAUCGAU  UGUGCAUUCG        50
GGAUUACGAU  CUUUCGACAG  GAGGCUCACA  ACAGGC                        86
```

( 2 ) INFORMATION FOR SEQ ID NO: 16:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 16:

```
GGGAGACAAG  AAUAAACGCU  CAAAUGACGU  CCGGAUCGAU  UGUGCAUUCG        50
GGAUUACGAU  CUUUCGACAG  GAGGCUCACA  ACAGGC                        86
```

( 2 ) INFORMATION FOR SEQ ID NO: 17:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 17:

```
GGGAGACAAG  AAUAAACGCU  CAAAUGACGU  CCUGAUCGAU  UGUGCAUUCG        50
GGGUUACGAU  CUUUCGACAG  GAGGCUCACA  ACAGGC                        86
```

( 2 ) INFORMATION FOR SEQ ID NO: 18:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 18:

```
GGGAGACAAG  AAUAAACGCU  CAAUUGACGU  CCUGAUCGAU  UGUGCAUUCG        50
GUGUGACGAU  CUUUCGACAG  GAGGCUCACA  ACAGGC                        86
```

( 2 ) INFORMATION FOR SEQ ID NO: 19:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 19:

GGGAGACAAG AAUAAACGCU CAAGUGACGU CCUGAUCGAU UGUGCAUUCG 50

GGGUUACGAU CUUUCGACAG GAGGCUCACA ACAGGC 86

( 2 ) INFORMATION FOR SEQ ID NO: 20:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 20:

GGGAGACAAG AAUAAACGCU CAAGUGACGU CCUGAUCGAU UGUGCAUUCG 50

GGGUUACGAU CUUUCGACAG GAGGCUCACA ACAGGC 86

( 2 ) INFORMATION FOR SEQ ID NO: 21:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 21:

GGGAGACAAG AAUAAACGCU CAAAUGACGC CCUGAUCGAU UGUGCAUUCG 50

GGGUUACGAU CUUUCGACAG GAGGCUCACA ACAGGC 86

( 2 ) INFORMATION FOR SEQ ID NO: 22:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 22:

GGGAGACAAG AAUAAACGCU CAAUGUGUCG UCCUGGUACG AUUUUGGUAU 50

AUAACCGUGG CUUUUCGACA GGAGGCUCAC AACAGGC 87

( 2 ) INFORMATION FOR SEQ ID NO: 23:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO: 23:

GGGAGACAAG AAUAAACGCU CAAUGUGUCG UCCUGGUACG AUUUUGGUAU 50

AUAACCGCGG CUUUUCGACA GGAGGCUCAC AACAGGC 87

( 2 ) INFORMATION FOR SEQ ID NO: 24:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear (i i) MOLECULE TYPE: RNA (genomic)

(x i) SEQUENCE DESCRIPTION: SEQ ID NO: 24:

```
GGGAGACAAG  AAUAAACGCU  CAACGUGUCG  UCCUGGUACG  AUUUUGGUAU           50

AUAACCGUGG  CUUUUCGACA  GGAGGCUCAC  AACAGGC                          87
```